(12) United States Patent
Thompson

(10) Patent No.: US 9,801,750 B2
(45) Date of Patent: Oct. 31, 2017

(54) LIMB PROTECTIVE COVERING

(75) Inventor: Ronnie Thompson, Rockwood, TN (US)

(73) Assignee: ALBAHEALTH, LLC, Rockwood, TN (US)

( * ) Notice: Subject to any disclaimer, the term of this patent is extended or adjusted under 35 U.S.C. 154(b) by 899 days.

(21) Appl. No.: 13/449,535

(22) Filed: Apr. 18, 2012

(65) Prior Publication Data
US 2012/0203152 A1    Aug. 9, 2012

Related U.S. Application Data

(63) Continuation-in-part of application No. 12/707,718, filed on Feb. 18, 2010, now abandoned.

(51) Int. Cl.
*A61F 5/00* (2006.01)
*A61F 5/01* (2006.01)

(52) U.S. Cl.
CPC ...................... *A61F 5/01* (2013.01)

(58) Field of Classification Search
CPC ......... A61F 5/01; A61F 13/041; A61F 13/043
USPC .............................. 602/3; 128/849, 856, 846
See application file for complete search history.

(56) References Cited

U.S. PATENT DOCUMENTS

| 3,983,870 | A | 10/1976 | Herbert et al. |
| 4,363,317 | A | 12/1982 | Broucek |
| 4,523,586 | A | 6/1985 | Couri |
| 4,562,834 | A | 1/1986 | Bates et al. |
| 5,016,648 | A | 5/1991 | Brown et al. |
| 5,063,919 | A | 11/1991 | Silverberg |
| 5,395,305 | A * | 3/1995 | Koide et al. ............ 602/48 |
| 5,592,953 | A | 1/1997 | Delao |
| 6,465,708 | B1 | 10/2002 | Augustine |
| 6,512,158 | B1 | 1/2003 | Dobos |
| 6,548,728 | B1 | 4/2003 | Faries, Jr. et al. |
| 7,290,290 | B2 | 11/2007 | Treadway Fancher et al. |
| 7,418,755 | B2 | 9/2008 | Bledsoe et al. |
| 7,762,968 | B1 * | 7/2010 | Hewitt .................. 602/3 |

* cited by examiner

*Primary Examiner* — Victoria J Hicks
(74) *Attorney, Agent, or Firm* — Baker, Donelson, Bearman, Caldwell & Berkowitz, PC; Dorian Kennedy

(57) ABSTRACT

A limb protective covering (10) includes an elongated sleeve (11) and an adjustable, elastic retaining strap (12). The sleeve has a closed end (15) and an open end (16) opposite the closed end. The sleeve is made of a high performance elastomeric polymer blend, such as a styrene-butadiene-styrene (SBS) based monolayer elastomeric antistatic film having a coefficient of friction of at least 0.6.

10 Claims, 1 Drawing Sheet

LIMB PROTECTIVE COVERING

REFERENCE TO RELATED APPLICATION

This is a continuation-in-part of U.S. patent application Ser. No. 12/707,718 filed Feb. 18, 2010.

TECHNICAL FIELD

This invention relates generally to limb protective coverings and more specifically to non-slip or slip resistant limb protective coverings.

BACKGROUND OF THE INVENTION

Heretofore, limb protective coverings have been designed in the form of an elongated tube in which the limb is positioned. A strap is placed about the open end of the tube to secure the tube to the limb. These protective coverings are typically utilized so that the limb with an injury, cast, or dressing may be kept dry when a person is bathing or showering.

While the elongated tube provides protection from moisture, a person with such a covering may slip or fall as a result of such.

Accordingly, it is seen that a need remains for a limb protective covering that restricts the slippage of an individual donning such. It is to the provision of such therefore that the present invention is primarily directed.

SUMMARY OF THE INVENTION

In a preferred form of the invention a limb protective covering comprises an elongated, tubular, flexible, and waterproof sleeve having a closed end and an open end opposite the closed end. The sleeve is made of a styrene-butadiene-styrene material. The protective covering also has a retaining member configured to fit about the sleeve when donned upon a limb.

DETAILED DESCRIPTION

Figure 1:
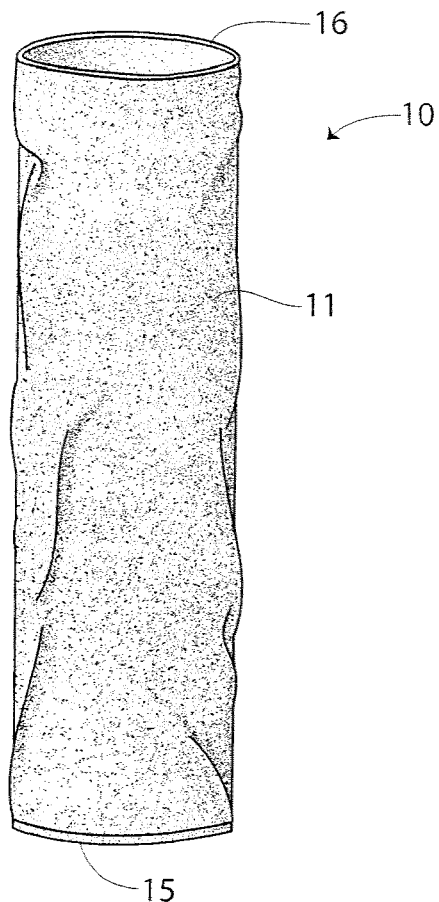
FIG. 1 is a perspective view of a preferred form of the limb protective covering in a preferred form of the invention.

With reference next to the drawings, there is shown a limb protective covering 10 in a preferred form of the invention. The limb protective covering 10 includes an elongated, tubular, flexible, waterproof sleeve 11 and an adjustable, elastic retaining strap 12. The sleeve 11 has a side wall with a closed end 15 and an open end 16 opposite the closed end 15. The sleeve 11 is made of a high performance elastomeric polymer blend, such as a styrene-butadiene-styrene (SBS) based monolayer elastomeric antistatic solid film. The sleeve 11 may be of various lengths and widths such as to end at different heights along the wearer's leg or arm L. The sleeve may, of course, be produced in any number of overall sizes to fit people of different sizes, or to fit different appendages or limbs.

The retaining strap 12 has a main body portion 18 and an adjustable retainer or buckle 19 through which the body portion 18 passes in an adjustable fashion. The strap 12 may be made of any elastized fiber, such as a polyester and spandex knit having an approximately 1 inch width. The buckle 19 is made of a plastic material, such as acetal, to adjust the sizing of the strap. The use of a buckle 19 is advantageous over the use of hook and loop type fasteners which degrade with dirt and water and thereby lose their retaining capabilities.

It has been discovered that a solid film of styrene-butadiene-styrene material increases the anti-skid capabilities of the limb protective covering. The increase in the anti-skid capabilities is illustrated by the following table showing the coefficient of friction associated with such.

TABLE 1

COEFFICIENT OF FRICTION TEST

|  | SBS | Poly-ethylene | approx. difference | approx. difference % |
|---|---|---|---|---|
| Static |  |  |  |  |
| Dry Surface Avg. | 0.952 | 0.417 | 0.54 | 56% |
| Std. Dev. | 0.186 | 0.069 |  |  |
| Kinetic |  |  |  |  |
| Dry Surface Avg. | 0.794 | 0.355 | 0.44 | 55% |
| Std. Dev. | 0.065 | 0.047 |  |  |
| Kinetic:Static ratio | 0.83 | 0.85 | −0.02 | −2% |
| Static |  |  |  |  |
| Wet Surface Avg. | 0.689 | 0.384 | 0.31 | 44% |
| Std. Dev. | 0.186 | 0.057 |  |  |
| Kinetic |  |  |  |  |
| Wet Surface Avg. | 0.729 | 0.339 | 0.39 | 53% |
| Std. Dev. | 0.065 | 0.031 |  |  |
| Kinetic:Static ratio | 1.06 | 0.88 | 0.18 | 17% |
| Gain/Loss on to Wet Surface |  |  |  |  |
| static | −0.263 | −0.033 |  |  |
|  | −21.6% | −7.9% |  |  |
| Kinetic | −0.065 | −0.016 |  |  |
|  | −8.2% | −4.5% |  |  |

The comparative test results appear in Table 1 where the SBS product is a limb protective covering 10 of the present invention, compared to a product made of a polyethylene material. The tabulated improvement was in the measured coefficient of friction of the limb protective covering. The SBS limb protective covering 10 of the present invention has a superior coefficient of friction in both Static and Kinetic testing and in both dry and wet conditions. The SBS product (covering 10) had a static dry measurement of 0.952 compared to the polyethylene product measurement of 0.417. This illustrates that the static coefficient of friction on a dry surface of the SBS product (covering 10) is over twice that of the polyethylene product, the actual difference being 0.54 which equates to a 56% difference. Similarly, the kinetic coefficient of friction on a dry surface of the SBS product (covering 10) is again over twice that of the polyethylene product, the actual difference being 0.44 which equates to a 55% difference. The test results also showed a vast improvement in the coefficient of friction as it relates to a wet condition. The static coefficient of friction on a dry surface of the SBS product (covering 10) is nearly twice that of the polyethylene product, the actual difference being 0.31 which equates to a 44% difference. Similarly, the kinetic coefficient of friction on a wet surface of the SBS product (covering 10) is again over twice that of the polyethylene product, the actual difference being 0.39 which equates to a 53% difference. This substantially higher coefficient of friction greatly improves the traction of the limb protective covering, thereby greatly reducing the potential of a person slipping on the underlying floor. The goal of reducing slippage is extremely desirous to healthcare, home care, and hospital facilities and the like as such may result in great bodily harm to the weak or elderly, or where normal gait has been affected and may result in greater liability to the medical facility. It should also be noted that the ratio of kinetic to static coefficient of friction exceeds 1.00, which means that the coefficient of friction when standing or moving the SBS material across a surface remains very high and in this case actually increases during movement, thereby providing excellent traction which was not obtained with similar prior art products.

This testing was conducted by Intertek of Pittsfield, Mass. utilizing a test standard of ASTM 1894-08 Coefficient of Friction on a linoleum surface utilizing an Instron series 5564 device.

Figure 2:
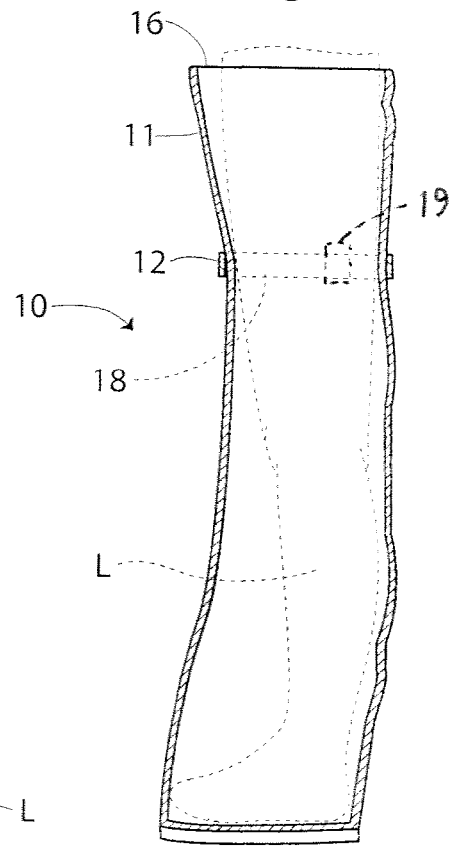
FIG. 2 is a perspective view of the limb protective covering of FIG. 1, shown donned upon a person's leg.
Figure 3:
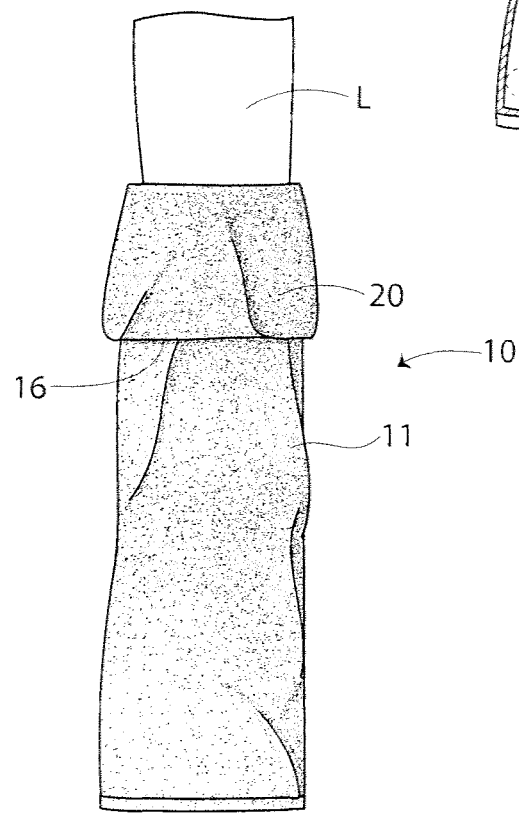
FIG. 3 is a perspective view of the limb protective covering of FIG. 1, shown donned upon a person's leg.

In use, the user inserts his or her leg into the open end 16 of the tubular sleeve 11 until the foot comes to rest against the closed end 15 of the sleeve. The example used herein is a leg, however, the limb protective covering may also be donned or worn upon an arm. Once the leg is inserted, the retaining strap 12 is placed about the leg, stretched, and tightened to form a snug fit about the leg, as shown in FIG. 2. The strap position is held in place through buckle 19. The portion of the sleeve extending above the retaining strap 12 may then be inverted about the strap to form an annular cuff or shingle 20 which aids in shedding water during a person's shower, as shown in FIG. 3.

The vast increase in the coefficient of friction relating to the use of the SBS material provides a great improvement over limb protective covering of the prior art. For instance, the increase coefficient of friction allows a covered leg to stay in place better while one stands within a bathtub or shower. Also, the increase improves traction while one steps out of the bath or shower or walks upon a floor, thereby restricting slippage upon the floor and a resulting fall. Also, when applied to an arm, one leaning on a shower wall is less likely to slide upon the wall which again may result in a fall.

The calculation of the coefficient of friction is dependant upon several factors, including the condition of the material, the exact composition of the materials, and the surface upon which it is calculated. The coefficient of friction of polyurethane is believed to be in the range of 0.2 to 0.3, the coefficient of friction of vinyl is believed to be in the range of 0.1 to 0.2, the coefficient of friction of nylon is believed to be approximately 0.48, and the coefficient of friction of nitrile is believed to be 0.06 to 0.25. These materials have been used for protective limb coverings in the past. A coefficient of friction of at least 0.6 is essential for purposes of the present invention. As such, a high performance elastomeric polymer blend, such as a styrene-butadiene-styrene (SBS) based monolayer elastomeric antistatic film, having a minimum coefficient of friction of 0.6 is preferred.

The solid film also provides an advantage over woven, knitted or like fabrics, which may or may not be treated with a coating to provide a water proofing capability. The solid film will not separate during use which would degrade the waterproofing capability, which may occur with fabrics over time or with the wearing of a protective coating.

It should also be noted that the tubular sleeve has a circumference (side wall) free of side seams, as only the closed end 15 includes a seam. Forming the sleeve without side seams insures that the sleeve is watertight and prevents the intrusion of water which may occur if a side seam fails, i.e., the side seam separates or otherwise becomes unbonded. This is especially true when the side wall or tube may be underfoot and thereby subject to the force and weight of a person which may cause a failure of a seam.

It thus is seen that a limb protective covering is now provided that provides greater non-skid capabilities. Although the covering has been illustrated and described in its preferred form, it should be understood that many modifications, additions and deletions may be made to that specific form without departure from the spirit and scope of the invention as set forth in the following claims.

The invention claimed is:

1. A limb protective covering comprising:
   an elongated, tubular, flexible, and waterproof sleeve having a closed end and an open end opposite said closed end, said elongated, tubular, flexible, and waterproof sleeve being made of a solid film of styrene-butadiene-styrene material, and
   a retaining member configured to fit about said elongated, tubular, flexible, and waterproof sleeve when donned upon a limb.

2. The limb protective covering of claim 1 wherein said retaining member is a stretchable strap.

3. The limb protective covering of claim 2 wherein said retaining member includes a buckle to adjust said strap.

4. The limb protective covering of claim 1 wherein said elongated, tubular, flexible, and waterproof sleeve does not include side seams.

5. The limb protective covering of claim 1 wherein said elongated, tubular, flexible, and waterproof sleeve has a circumference free of seams.

6. A limb protective covering comprising:
   an elongated, tubular, flexible, and waterproof sleeve having a closed end and an open end opposite said closed end, said elongated, tubular, flexible, and waterproof sleeve being made of a solid film of styrene-butadiene-styrene material, and
   a retaining member configured to be coupled to said elongated, tubular, flexible, and waterproof sleeve when donned upon a limb to maintain said sleeve in position.

7. The limb protective covering of claim 6 wherein said retaining member is a stretchable strap.

8. The limb protective covering of claim 7 wherein said retaining member includes a buckle to adjust the strap.

9. The limb protective covering of claim 6 wherein said elongated, tubular, flexible, and waterproof sleeve does not include side seams.

10. The limb protective covering of claim 6 wherein said elongated, tubular, flexible, and waterproof sleeve has a circumference free of seams.

* * * * *